United States Patent [19]

Stewart et al.

[11] Patent Number: 4,793,180

[45] Date of Patent: Dec. 27, 1988

[54] DELAYED ACTION IRREVERSIBLE HUMIDITY INDICATOR

[75] Inventors: Roger K. Stewart, Tucson, Ariz.; James R. Blinn, Riverside, Calif.

[73] Assignees: AGM Cargo-Ties, Inc., Tucson, Ariz.; Humidial Corporation, Colton, Calif.

[21] Appl. No.: 587,369

[22] Filed: Mar. 8, 1984

Related U.S. Application Data

[63] Continuation of Ser. No. 311,391, Oct. 14, 1981, abandoned.

[51] Int. Cl.⁴ .............................................. G01N 25/56
[52] U.S. Cl. ............................................ 73/335; 73/73
[58] Field of Search ................... 116/200, 206; 73/336, 73/335, 29, 73; 422/56, 57

[56] References Cited

U.S. PATENT DOCUMENTS

| | | | |
|---|---|---|---|
| 2,214,354 | 9/1940 | Snelling | 116/114 |
| 2,249,867 | 7/1941 | Snelling | 73/335 |
| 2,716,338 | 8/1955 | Blinn | 73/335 |
| 2,787,238 | 4/1957 | Luce | 116/114 |
| 2,876,321 | 3/1959 | Amdur | 201/63 |
| 3,198,163 | 8/1965 | Williams | 116/206 |
| 3,425,388 | 2/1969 | West | 73/73 |
| 3,680,364 | 8/1972 | Carrier | 73/73 |
| 3,788,128 | 1/1974 | Strohecker | 73/73 |
| 3,816,575 | 6/1974 | Susuki | 106/86 |
| 3,898,172 | 8/1975 | Reif | 73/335 |
| 4,034,609 | 7/1977 | Fuller | 73/335 |
| 4,063,452 | 12/1977 | Bradshaw | 116/206 |
| 4,098,120 | 7/1978 | Manske | 73/335 |
| 4,150,570 | 4/1979 | Fuller | 73/335 |
| 4,195,058 | 3/1980 | Patel | 422/56 |

OTHER PUBLICATIONS

"Relative Humidity and Concrete Curing", Battelle Development Corporation (brochure), copyright 1983.
"Flow of Fluids Through Porous Materials" by Collins, pp. 1-11, copyright 1961.

Primary Examiner—William A. Cuchlinski, Jr.
Attorney, Agent, or Firm—Cahill, Sutton & Thomas

[57] ABSTRACT

An irreversible humidity indicator having a delayed response time includes a porous plastic carrier having upper and lower opposing surfaces, the upper surface including a depressed region for containing a deliquescent agent coated with a water soluble dye. A sheet of blotter paper overlies the upper surface of the porous plastic carrier and contacts the dye-coated deliquescent agent for absorbing the water soluble dye, and thereby providing an irreversible indication, when the humidity level directly surrounding the deliquescent agent is sufficiently high to dissolve the deliquescent agent. The plastic porous carrier is packaged to isolate the upper surface thereof from direct exposure to the environment to be monitored, and the density and thickness of the plastic porous carrier are selected to delay the passage of moisture-laden air from the lower surface to the depressed region thereof for a predetermined time.

12 Claims, 1 Drawing Sheet

DELAYED ACTION IRREVERSIBLE HUMIDITY INDICATOR

This is a continuation of application Ser. No. 311,391 filed Oct. 14, 1981, now abandoned.

BACKGROUND OF THE INVENTION

1. Field of the Invention

The present invention relates generally to indicators used to monitor the humidity of an environment, and more particularly, to a humidity indicator which provides an irreversible indication that a predetermined humidity level has been reached while substantially delaying the reaction time of such an indicator.

2. Description of the Prior Art

When shipping or storing corrosion-susceptible equipment, such as electronic and military related equipment, it is desirable to know whether the interior of containers used to ship or store such equipment has been exposed to humidity levels sufficient to cause corrosion of components within such equipment.

Humidity indicators which reversibly change colors in response to the surrounding humidity level are generally known in the art. Such prior art reversible humidity indicators typically utilize cobalt chloride as the indicator material, and the prevailing level of humidity determines the color of the indicator material at any particular time. Military specifcations have been developed regarding the packaging, colors, an other features of such humidity indicators, for example, military specification number MIL-I-26860.

However, there is a need, particularly in military applications, to detect the occurrence of a predetermined level of humidity and to indicate the same without allowing the indication to reverse itself after humidity levels have dropped. Were a long term storage container, stored within a relatively warm climate, to develop an air leak, moisture could enter the container during periods of relatively high humidity in the vicinity of the container. Upon subsequent cooling of the container, admitted moisture may condense and cause corrosion of the equipment stored within the container. Subsequent warming and drying of the air external to and surrounding the container can subsequently draw out all of the moisture previously admitted into the container. Thus, a reversible type humidity indicator will fail to indicate the temporary presence of high humidity levels within the container for durations sufficiently long to cause corrosion.

In view of the above mentioned disadvantages of reversible type humidity indicators, irreversible humidity indicators have been developed and are known in the art. For example, U.S. Pat. No. 2,214,354 discloses an irreversible humidity indicating device wherein a deliquescent agent such as calcium chloride is mixed with a water soluble dye, and the mixture is disposed upon a porous surface such as a sheet of absorbent paper. Upon being exposed to a predetermined humidity level, the deliquescent agent liquifies and dissolves the dye; the dye solution is carried by capillary action into the porous surface or paper for producing a permanent and irreversible marking. The aforementioned patent further describes various deliquescent agents which may be alternately employed for indicating different humidity levels.

Shipping containers and long term storage containers for corrosion-susceptible equipment are usually packed with a desiccant to dehydrate the area enclosed by the container after it is sealed. Periodically, such containers are opened to recharge or replace the desiccant packed within each such container. After recharging or replacing the desiccant, the container is again sealed. Sufficient quantities of desiccant are typically packed within each such container to ensure that the space enclosed by the container is dehydrated to safe levels within approximately one hour or less after the container is seal However, in the event that the container is surrounded by relatively humid environment either during the initial operation of storing the equipment within the container or during subsequent operations to recharge or replace the desiccant within the container, the irreversible humidity indicator of the type disclosed by the aforementioned patent may be prematurely actuated due to the temporarily high humidity levels within the container both before the container is sealed and also during the interval after sealing while the desiccant initially dehydrates the interior of the container. For example, at 85 percent relative humidity, it may take only 15 to 30 minutes to activates such an irreversible humidity indicator. Such premature actuation requires removal of the irreversible humidity indicator initially present and replacement with a fresh irreversible humidity indicator.

Accordingly, it is an object of the present invention to provide an irreversible humidity indicator adapted to monitor humidity levels within long term storage containers or the like wherein the response time of the indicator is substantially delayed over that of presently known irreversible humidity indicators to facilitate the initial packaging of corrosion-susceptible equipment within such containers and to facilitate the subsequent opening of such containers to replace or recharge desiccant therein without prematurely actuating the indicator.

It is a further object of the present invention to provide such an irreversible humidity indicator adaptable to existing humidity indicator packaging and mounting techniques.

It is yet another object of the present invention to provide such an irreversible humidity indicator which may be manufactured easily and inexpensively.

These and other objects of the present invention will become more apparent to those skilled in the art as the description thereof proceeds.

SUMMARY OF THE INVENTION

Briefly described, and in accordance with one embodiment thereof, the present invention relates to an irreversible humidity indicator having a delayed response time and including a porous carrier having upper and lower opposing surfaces, the upper surface including a depressed region or pocket for receiving a deliquescent agent coated with a water soluble dye, and further including a layer of absorbent material overlying the upper surface of the porous carrier for absorbing the water soluble dye when the humidity level within the depressed region is sufficiently high to dissolve the dye-coated deliquescent agent. The density and thickness of the porous carrier are selected to delay the passage of moisture-laden air from the lower surface of the porous carrier to the depressed region for a time period at least as great as the time period normally required to dissolve the deliquescent agent upon direct exposure to such moisture-laden air; preferably the density and thickness of the porous carrier are sufficient to delay the passage of moisture-laden air from the lower surface of the porous carrier to the depressed region for at least thirty minutes even when the relative humidity level of such moisture-laden air approaches 85 percent at room temperature.

In the preferred embodiment of the present invention, a housing is provided for isolating the upper surface of the porous carrier from direct exposure to moisture-laden air within the enclosed space to be monitored while allowing the lower surface of the porous carrier to be directly exposed to such moisture-laden air. The housing preferably has a threaded body to facilitate mounting the irreversible humidity indicator within a wall bounding the enclosed space and includes a transparent cover extending over the layer of absorbent material for allowing the same to be viewed external from the enclosed space.

DESCRIPTION OF THE PREFERRED EMBODIMENT

Figure 1:
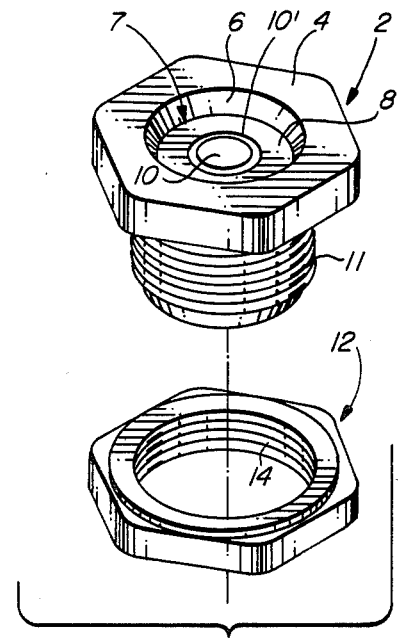
FIG. 1 is a perspective view of a delayed action irreversible humidity indicator including a housing which may be engaged by a nut for securing the irreversible humidity indicator to a wall of a container.

Shown in FIG. 1 is a preferred embodiment of a delayed action irreversible humidity indicator constructed according to the teachings of the present invention and including a housing generally designated 2. Housing 2 includes a hex-shaped head portion 4 having a central bore 6 extending therethrough. Bore 6 is sealingly engaged by a transparent window 7, shown more clearly in FIG. 4, which is preferably made of plexiglass. Visible within FIG. 1 below window 7 is a circular sheet of blotter paper or other absorbent material, the function of which will be described more fully below. Also visible upon blotter paper 8 is a centrally located indicator portion 10 defined by a ring 10' printed upon blotter paper 8.

Figure 2:
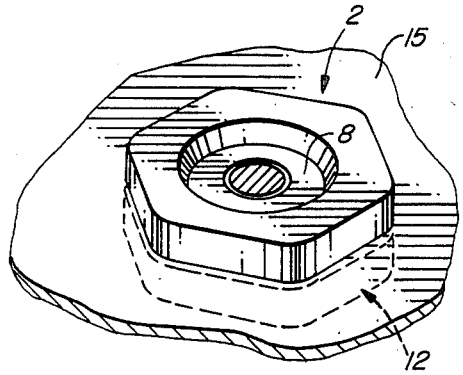
FIG. 2 is a partial perspective view of the delayed action irreversible humidity indicator shown in FIG. 1 after being secured to the wall of a container.

Extending from head portion 4 of housing 2 is an externally threaded body portion 11 having a length sufficient to extend through an aperture within a wall of a container or other enclosed space to be monitored. Also shown in FIG. 1 is a hex-shaped nut 12 having an internally threaded bore 14 for engaging externally threaded body portion 11 of housing 2. As shown in FIG. 2, nut 12 may be used to threadedly engage housing 2 for securing the same within an aperture formed within wall 15. Housing 2 and nut 12 are preferably of anodized aluminum construction. Further details concerning thread sizes and other features of housing 2 may be determined by consulting U.S. Military Specification No. MIL-I-26860, which specification is hereby incorporated by reference.

Figure 3A:
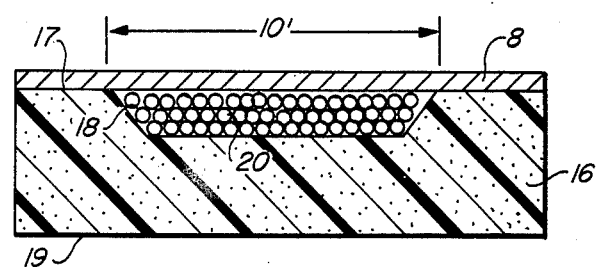
FIGS. 3A and 3B are cross-sectional views of the operative portion of the delayed action irreversible humidity indicator illustrating its condition both before and after, respectively, continuous exposure to relatively high humidity for a number of hours.
Figure 3B:
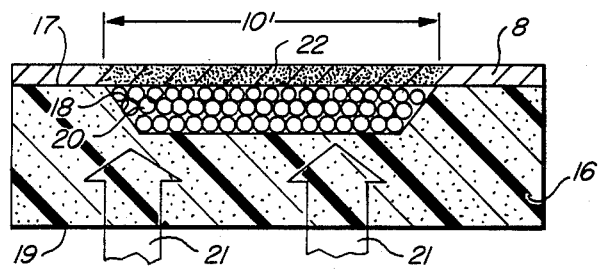

Referring now to FIGS. 3A and 3B, the operative portion of the delayed action irreversible humidity indicator is shown in cross-section. A plastic porous carrier 16 includes an upper surface 17 and an opposing lower surface 19. Upper surface 17 includes a depressed region or pocket 18 for containing an alkali metal salt or other deliquescent agent coated with a water soluble dye. In the preferred embodiment of the present invention, sodium chloride crystals are used as the deliquescent agent and are coated with a brilliant orange dye. Blotter paper 8 or a sheet of similar absorbent material overlies upper surface 17 of plastic porous carrier 16, and central portion 10 of blotter paper 8 extends directly above and in contact with the dye-coated deliquescent agent 20. Preferably, blotter paper 8 is white or a light color to increase the contrast between the color of central region 10 before and after being stained by the water soluble dye and thereby allowing an observer to more easily perceive the condition of the indicator.

Upon exposure of lower surface 19 to moisture-laden air, such moisture-laden air begins to permeate the pores of plastic porous carrier 16, as designated by arrows 21 in FIG. 3B. After a predetermined delay period, the moisture-laden air reaches the depressed region 18 and surrounds dye-coated deliquescent agent 20. When the humidity level within depressed region 18 reaches a predetermined level, deliquescent agent 20 begins to liquify and form a water soluble dye solution. The orange dye within the solution is then absorbed by central portion 10 of blotter paper 8 for providing an irreversible indication 22 that the humidity level of the air within the enclosed space being monitored has exceeded predetermined minimum relative humidity level for a predetermined continuous period of time.

As mentioned above, the particular relative humidity level at which the humidity indicator is actuated is determined by the selection of the particular deliquescent agent 20. For example, if sodium chloride crystals are used as the deliquescent agent, then humidity level below approximately 55 percent relative humidity will not actuate the indicator, regardless of duration. When humidity levels within the enclosed space are approximately equal to or exceed 55 percent relative humidity, the time delay provided by the plastic porous carrier 16 is determined by the density and thickness thereof. In the preferred embodiment of the present invention, high density porous polyethylene plastic material of the type commercially available from the Porex Division of Glass Rock Products, Inc. of Fairborne, Ga., sold under the trademark "POREX", is used as the plastic porous carrier material 16.

It has been found that if such high density porous polyethylene plastic is used as carrier 16, and if the distance between lower surface 19 and depressed region 18 is approximately 0.1 inch, then the irreversible humidity indicator device must be continuously exposed to 55 percent relative humidity for approximately an eight hour period, or alternatively, to 85 percent relative humidity continuously for approximately a two hour period, before the sodium chloride crystals will liquify and carry the water soluble dye into blotter paper 8. In contrast, were such dye-coated sodium chloride crystals to be exposed directly to 55 percent relative humidity air, blotter paper 8 would be stained in two hours or less; were the sodium chloride crystals exposed directly to 85 percent relative humidity air, the blotter paper would be stained within fifteen to thirty minutes.

Thus, by interposing porous plastic carrier 16 between the sodium chloride crystals and the moisture-laden air within the enclosed space being monitored, the response time of the irreversible indicator device is substantially delayed. Typically, during initial packaging and subsequent desiccant recharging operations, the humidity indicator would not purposely be exposed to humidity levels much above 85 percent relative humidity at room temperature for periods which exceed thirty minutes. Accordingly, the aforementioned delays provided by porous plastic carrier 16 are sufficiently long to allow for packaging of the corrosion-susceptible equipment within long term storage containers and to allow for periodic opening of such containers to recharge the desiccant therein without prematurely being actuated.

Figure 4:
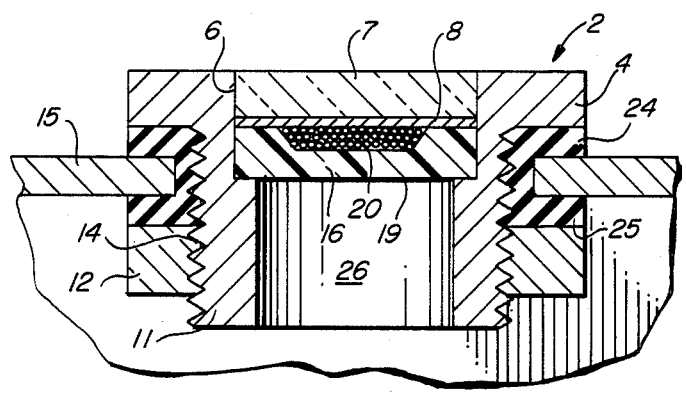
FIG. 4 is a cross-sectional view of the delayed action irreversible humidity indicator of the present invention mounted to the wall of a container.

Referring now to FIG. 4, the preferred embodiment of the present invention is shown mounted to a wall 15 of a container enclosing a space to be monitored. An aperture is formed within wall 15, and externally threaded body portion 11 is inserted through the aperture. A gasket 24 seals head portion 4 of housing 2 against the outer surface of wall 15. Nut 12 is threadedly engaged over externally threaded body portion 11 of housing 2, and a second gasket 25 is inserted between nut 22 and the inner surface of wall 15 for effecting an additional seal therebetween. As shown in FIG. 4, porous plastic carrier 16 is situated directly below plexiglass window 7. Externally threaded body portion 11 includes a central bore 26 for exposing lower surface 19 of porous plastic carrier 16 to the space enclosed by wall 15. The periphery of porous plastic carrier 16 sealingly engages central bore 6 within head portion 4 to isolate upper surface 17 of plastic porous carrier 16 from direct exposure to moisture-laden air within bore 26.

Figure 5:
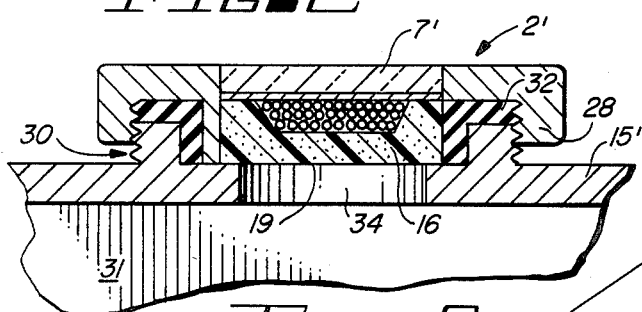
FIG. 5 is a cross-sectional view of a delayed action irreversible humidity indicator including a modified housing having an internally threaded, downwardly turned flange for engaging an externally threaded portal of a container.

FIG. 5 illustrates an alternate embodiment of the irreversible humidity indicator housing wherein housing 2' includes a downwardly turned flange 28 at the outer periphery thereof. Flange 28 is internally threaded for engaging an externally threaded portal 30 formed upon wall 15' of the container 31. Gasket 32 effects an airtight seal between housing 2' and portal 30. Portal 30 includes an aperture 34 for exposing moisture-laden air within container 31 to lower surface 19 of plastic porous carrier 16.

Figure 6:
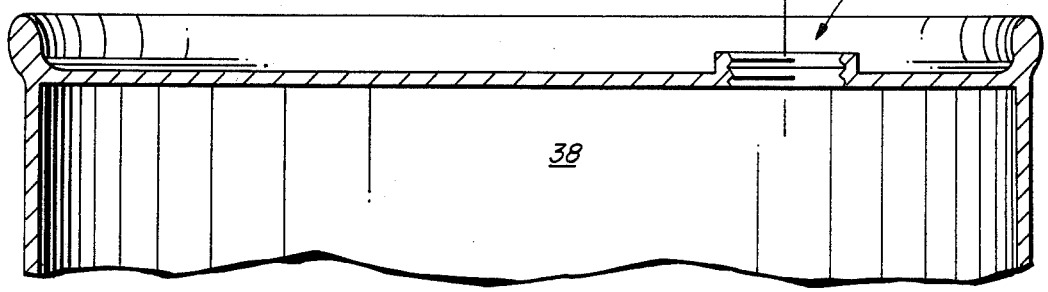
FIG. 6 is a cross-sectional view of the delayed action irreversible humidity indicator shown in FIG. 1 and illustrating the manner in which the indicator housing may be engaged by an internally threaded portal of a storage container.

FIG. 6 illustrates another application of the present invention wherein housing 2 of FIG. 1 threadedly engages an internally threaded portal 36 of a storage container 38, such as a conventional 55 gallon drum. Gasket 24 is inserted between head portion 4 of housing 2 and portal 36 for forming an airtight seal therebetween.

Those skilled in the art will now appreciate that a delayed action irreversible humidity indicator has been described which avoids premature actuation due to temporary exposure to relatively high humidity conditions during initial packaging of long term storage containers and during periodic desiccant recharging operations. While the present invention has been described with regard to a preferred embodiment thereof, the description is for illustrative purposes only and is not to be construed as limiting the scope of the invention. Various modifications and changes may be made by those skilled in the art without departing from the true spirit and scope of the invention as defined by the appended claims.

We claim:

1. An irreversible humidity indicator having a delayed response time for monitoring humidity levels within an enclosed space, comprising in combination:
   a. a porous plastic carrier having and lower opposing surfaces, said upper surface including a depressed region;
   b. isolating means for isolating said upper surface from direct exposure to moisture-laden air within the enclosed space while allowing said lower surface to be directly exposed to such moisture-laden air;
   a. a deliquescent agent coated with a water soluble dye disposed within the depressed region of said upper surface;
   d. a layer of absorbent sheet material overlying said upper surface of said porous carrier and directly above said dye-coated deliquescent agent for absorbing said water soluble dye when the humidity level within said depressed region is sufficiently high to dissolve said dye-coated deliquescent agent; and
   e. said porous plastic carrier being of a sufficient density and thickness to delay the passage of moisture-laden air within the enclosed space to said depressed region for a time period greater than the time period normally required to dissolve said deliquescent agent upon direct exposure to such moisture-laden air.

2. An irreversible humidity indicator as recited by claim 1 wherein said porous plastic carrier delays the passage of moisture-laden air from the enclosed space to said depressed region for at least thirty minutes when said moisture-laden air has a relative humidity level of 85 percent at room temperature.

3. An irreversible humidity indicator as recited by claim 1 wherein said porous plastic material is high density porous polyethylene plastic having a thickness of approximately one-tenth inch.

4. An irreversible humidity indicator as recited by claim 1 wherein said layer of absorbent material is a sheet of blotter paper.

5. An irreversible humidity indicator as recited by claim 1 wherein said deliquescent agent comprises sodium chloride crystals.

6. An irreversible humidity indicator as recited by claim 1 wherein said isolating means comprises a housing having an externally threaded cylindrical body adapted to be inserted through a wall bounding the enclosed space, said irreversible humidity indicator further including a nut for threadedly en gaging said housing to secure said housing to said wall, said housing including a transparent, sealed cover extending over said layer of absorbent material for allowing the same to be viewed external from the enclosed space.

7. An irreversible humidity indicator as recited by claim 1 wherein said isolating means comprises a housing having an externally threaded cylindrical body adapted to engage a threaded bore within a wall bounding the enclosed space, said housing including a transparent, sealed cover extending over said layer of absorbent material for allowing the same to be viewed external from the enclosed space.

8. An irreversible humidity indicator having a delayed response time, comprising in combination:
   a. a porous plastic carrier having upper and lower opposing surfaces, said upper surface including a depressed region;
   b. a deliquescent agent coated with a water soluble dye disposed within the depressed region of said upper surface;
   c. a layer of an absorbent material disposed over said upper surface of said porous plastic carrier for absorbing said water soluble dye when the humidity level within said depressed region is sufficiently high to dissolve said dye-coated deliquescent agent; and
   d. said porous plastic carrier being of a sufficient density and thickness to delay the passage of moisture-laden air from said lower surface to said depressed region for a time period greater than the time period normally required to dissolve said deliquescent agent upon direct exposure to such moisture-laden air.

9. An irreversible humidity indicator as recited by claim 8 wherein said porous carrier relays the passage of said moisture-laden air from said lower surface to said depressed region for at least thirty minutes when said moisture-laden air has a relative humidity level of 85 percent at room temperature.

10. An irreversible humidity indicator as recited by claim 8 wherein said porous plastic material is high density porous polyethylene plastic.

11. An irreversible humidity indicator as recited by claim 8 wherein said layer of absorbent material is a sheet of blotter paper.

12. An irreversible humidity indicator as recited by claim 8 wherein said deliquescent agent comprises sodium chloride crystals.

* * * * *